United States Patent [19]

Morita et al.

[11] Patent Number: 5,151,521

[45] Date of Patent: Sep. 29, 1992

[54] 1-AMINOETHYL PHOSPHONIC ACID DERIVATIVES

[75] Inventors: Yoshiharu Morita; Haruyuki Chaki, both of Yokohama; Yasuo Hoshide, Okegawa; Junko Takashima, Yokohama, all of Japan; Arthur A. Patchett, Westfield, N.J.

[73] Assignee: Merck & Co., Inc., Rahway, N.J.

[21] Appl. No.: 714,423

[22] Filed: Jun. 12, 1991

Related U.S. Application Data

[60] Division of Ser. No. 529,698, May 24, 1990, Pat. No. 5,061,806, which is a continuation of Ser. No. 211,658, Jun. 27, 1988, abandoned.

[30] Foreign Application Priority Data

Jul. 6, 1987 [JP] Japan .................................. 610354

[51] Int. Cl.$^5$ ................................. C07F 9/40
[52] U.S. Cl. ................................ 548/112; 548/413; 548/414; 558/170; 558/172; 558/174
[58] Field of Search .................. 548/112, 413, 414; 558/170, 172, 174

*Primary Examiner*—Mary C. Lee
*Assistant Examiner*—Michael G. Ambrose
*Attorney, Agent, or Firm*—Frank P. Grassler; Joseph F. DiPrima

[57]  ABSTRACT

New phosphonic acid derivatives are described which display antibacterial activity.

4 Claims, No Drawings

1-AMINOETHYL PHOSPHONIC ACID DERIVATIVES

This is a division of application Ser. No. 529,698, filed May 24, 1990, now U.S. Pat. No. 5,061,806, which is a continuation of application Ser. No. 211,658, filed Jun. 27, 1988, now abandoned.

BACKGROUND OF THE INVENTION

1. Field of the Invention

This invention relates to new antibacterial agents which interfere in bacterial cell wall synthesis.

2. Brief Description of the Art

Many antibacterial agents owe their selective toxicity to the fact that their targets are structures which are only present in the sensitive bacterium. One of these structures is peptidoglycan a cell wall polymer which plays a vital role in protecting bacteria from lysis. A number of agents, e.g., $\beta$-lactams, bacitracin, and flavomycin, interfere with the assembly of this polymer by inhibiting enzymatic reactions involved in the final stages of assembly.

Peptidoglycan biosynthesis involves a precursor, UDP-MurNAc-Ala-D-Glu-Lys-D-Ala-D-Alanine that is biosynthesized in a multienzyme pathway which terminates in the addition of D-Alanine-D-Alanine to the UDP-MurNAc tripeptide. The formation of D-Alanyl-D-Alanine is catalyzed by D-Alanyl-D-Alanine ligase (synthetase). It is known that inhibition of D-Alanyl-D-Alanyl ligase will terminate peptido glycan biosynthesis resulting in vivo in bacterial cell lysis. Such inhibitors can serve as antibacterials. For example, D-Cycloserine, a D-Alanine mimic, is a reversible inhibitor of the ligase at both the donor and acceptor sites and is the most potent ligase inhibitor described heretofore, and is a potent antibacterial. (F. C. Neuhaus et al., *Biochemistry* 3, 471–480(1964)).

Dipeptide analogs of D-Alanyl-D-Alanine are also known to be inhibitors of ligase. (F. C. Neuhaus et al., *Biochemistry* 8, 5119–5124 (1965), and F. C. Neuhaus and W. P. Hammes, *Pharmac. Ther.* 14, 265–319 (1981)).

With this background, the search for newer and more effective antibacterial agents which are ligase inhibitors, is a continuing one.

SUMMARY OF THE INVENTION

It has been found that compounds of Structure I shown below, are inhibitors of bacterial cell wall synthesis, and are useful in the treatment of bacterial infections.

By this invention there is provided a phosphonic acid derivative represented by the general formula (I)

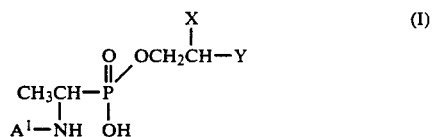

wherein $A^1$ is a hydrogen atom, an amino acid or oligopeptide residue optionally having a protecting group which is obtained by removing, from an amino acid or oligopeptide optionally having a protecting group, the hydroxyl group of the terminal carboxyl group, or a protecting group for the amino group; X is (a) a hydroxyl group,

wherein $R^1$ is an alkyl group, or (c) $-NHA^2$, wherein $A^2$ is a hydrogen atom, an amino acid or oligopeptide residue optionally having a protecting group which is obtained by removing from an amino acid or oligopeptide optionally having a protecting group, the hydroxyl group of the terminal carboxyl group, or a protecting group for the amino group; and Y is (a) $-CH_2OH$,

wherein $R^2$ is an alkyl group, or $$\underset{C-B}{\overset{O}{\|}} \quad (c)$$

wherein B is a hydroxyl group, an amino acid or oligopeptide residue optionally having a protecting group obtained by removing, from an amino acid or oligopeptide optionally having a protecting group, the hydrogen atom of the terminal amino group, or a protecting group for the carboxyl group.

Also provided is a pharmaceutical composition useful in the treatment of antibacterial infections which comprises a pharmaceutically acceptable carrier and a pharmaceutically effective amount of an antibacterial compound of formula I.

Also provided is a method for treating a bacterial infection in a mammalian host comprising administering to said host a therapeutically effective amount of the above described composition.

DETAILED EXPLANATION OF THE INVENTION

The present invention relates to phosphonic acid derivatives.

Of the phosphonic acid derivatives represented by the general formula (I) of the present invention, the compounds having no protecting group are valuable as an inhibitor to the biosynthesis of bacterial cell walls. They are further useful, together with the compounds having a protecting group, as an intermediate for the synthesis of more valuable anti-bacterial substances.

Of the phosphonic acid derivatives represented by the general formula (I) of the present invention, the compounds having no protecting group may take a form of an intramolecular salt but may also form a salt with other acid or base. As such a salt, the amine salt includes salts with mineral acids, e.q. hydrochloric acid, hydrobromic acid, sulfuric acid) or with organic acids, and the carboxylic acid or phosphonic acid salts include salts with alkali metals or alkaline earth metals, e.g. sodium, potassium, calcium, magnesium, ammonium salts and organic amine salts.

In the general formula (I), as the amino acid when $A^1$ is an amino acid or oligopeptide residue optionally having a protecting group, there can be mentioned glycine, alanine, valine, norvaline, leucine, isoleucine, serine, threonine, phenylalanine, tyrosine, tryptophane, histidine, aspartic acid, asparagine, glutamic acid, glutamine, lysine, arginine, cysteine, methionine, proline, etc. Preferably, there can be mentioned glycine, alanine, valine, norvaline, leucine, isoleucine, serine, cysteine, methionine, etc. As the oligopeptide, there can be mentioned oligopeptides constituted of 2 to 10, preferably 2 to 5 of the above mentioned amino acids which may be the same or different. In amino acids including those constituting oligopeptides, there exist optical isomers. The configuration can be any of L-, D- and DL-forms. L-amino acids are used in most cases. As the protecting group for the amino groups, there can be mentioned protecting groups commonly used in peptide chemistry, such as aralkyloxycarbonyl groups optionally having a substituent, e.g. carbobenzoxy, p-methoxybenzyloxycarbonyl, p-nitrobenzyloxycarbonyl, p-chlorobenzyloxycarbonyl, p-bromobenzyloxycarbonyl, p-methylbenzyloxycarbonyl, $C_1$-$C_5$ lower alkoxy-carbonyl groups, being optionally substituted, e.g. tert-butoxycarbonyl, 2,2,2-trichloroethoxycarbonyl and trityl group. As the protecting group for the carboxyl group, there can be mentioned protecting groups commonly used in peptide chemistry, such as $C_1$-$C_5$ lower alkoxy groups, e.g. methoxy, ethoxy, propoxy, tert-butoxy, lower alkoxy groups having a substituent, e.q. methoxymethyloxy, acetoxymethyloxy, pivaloyloxymethyloxy, benzyloxy, p-nitrobenzyloxy, p-methoxybenzyloxy, phthalidyloxy and aryloxy groups optionally having a substituent e.g. phenyloxy, indanyloxy. As $R^1$ (an alkyl group) when X is the case (b), there can be mentioned straight chain or branched chain alkyl groups of 1 to 30 carbon atoms. As $A^2$ (an amino acid or oligopeptide residue optionally having a protecting group) when X is the case (c), there can be mentioned amino acid or oligopeptide residues optionally having the protecting groups of $A^1$ which may be the same or different. As the protecting group for the amino group, there can be mentioned protecting groups for the amino groups of amino acid or oligopeptide residues optionally having the protecting groups of $A^1$ which may be the same or different. As $R^2$ (an alkyl group) when Y is the case (b), there can be mentioned straight chain or branched chain alkyl groups of 1 to 30 carbon atoms. As B (an amino acid or oligopeptide residue optionally having a protecting group) when Y is the case (c), there can be mentioned amino acid or oligopeptide residue optionally having the protecting groups of $A^1$ which may be the same or different. As the protecting group for the carboxyl group, there can be mentioned protecting groups for the carboxyl groups of amino acid or oligopeptide residues optionally having the protecting groups $A^1$ which may be the same or different.

Hence, the following compounds can be mentioned as specific examples of the phosphonic acid derivatives of the present invention:

1. 2,3-Dihydroxypropyl (1RS)-1-aminoethylphosphonate hydrochloride
2. 2,3-Dihydroxypropyl (1RS)-1-(L-alanylamino)ethylphosphonate hydrochloride
3. 2,3,-Dipalmitoyloxypropyl (1RS)-1-carbobenzoxyaminoethylphosphonate
4. 2,3-Dipalmitoyloxypropyl (1RS)- 1-aminoethylphosphonate
5. (2R)-2-Carbobenzoxyamino-2-(p-nitrobenzyloxycarbonyl)-ethyl (1RS)-1-carbobenzoxyaminoethylphosphonate
6. (2R)2-Amino2-carboxyethyl (1RS)-1-aminoethylphosphonate monohydrochloride
7. (2S)-2-(tert-Butoxycarbonylamino)-2-[(1S)-1-tert-butoxycarbonylethylaminocarbonyl]ethyl (1RS)-1-carbobenzoxyaminoethylphosphonate
8. (2S)-2-Amino-2[(1S)-1-carboxyethylaminocarbonylethyl](1RS)-1-aminoethylphosphonate monohydrobromide
9. (2S)-2-(tert-Butoxycarbonyl-L-alanylamino)-2-(tert-Butoxycarbonyl)ethyl (1RS)-1-carbobenzoxyamino ethylphosphonate
10. (2S)-2-(1-alanylamino)-2-carboxylethyl (1RS)-1-aminoethylphosphonate monohydrobromide The present invention will be described more in detail by explaining the typical processes for producing the present compounds. However, the present invention is in no way restricted to these processes.

The following processes A, B and C can be mentioned as the typical processes for producing the present compounds.

Process A

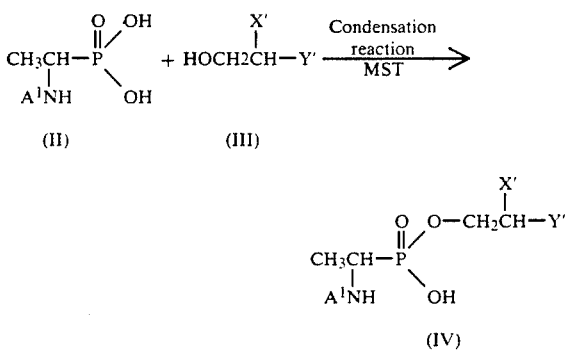

[wherein $A^1$ has the same definition as the $A^1$ of the general formula (I) with a proviso that hydrogen atom is not included and the amino acid or oligopeptide residue has a protecting group; $X^1$ has the same definition as the X of the general formula (I) with a proviso that (1) the hydroxyl group of the case (a) has a protecting group and (2) the $A^2$ of the case (c) includes no hydrogen atom and the amino acid or oligopeptide residue has a protecting group; and $Y^1$ has the same definition as the Y of the general formula (I) with a proviso that (1) the group —$CH_2OH$ of the case (a) has a protecting group and (2) the B of the case (c) includes no hydroxyl group and the amino acid or oligopeptide residue has a protecting group].

In this process, a phosphonic acid represented by the general formula (II) and an alcohol represented by the general formula (III) are subjected to a condensation reaction in the presence of a condensation agent to obtain a desired phosphonic acid derivative represented by the general formula (IV).

This reaction can be effected by utilizing a known method, for example, a condensation reaction used in the production of 5'-o-(1-aminoethane-1-phosphonyl)uridine or adenosine [K. Lesiak, W. J. Stec, W. S. Zielinski, Polish J. Chem. 53 327 (1979)]. Explaining a typical case, a phosphonic acid represented by the general formula (II) and an alcohol represented by the general formula (III) are reacted for a long time at room temperature in the presence of anhydrous pyridine using mesitylenesulfonyl triazolide as a condensation agent, whereby a triazole salt of a phosphonic acid derivative is produced. A desired phosphonic acid derivative is obtained by treating the triazole salt with dilute hydrochloric acid to remove triazole.

Process B

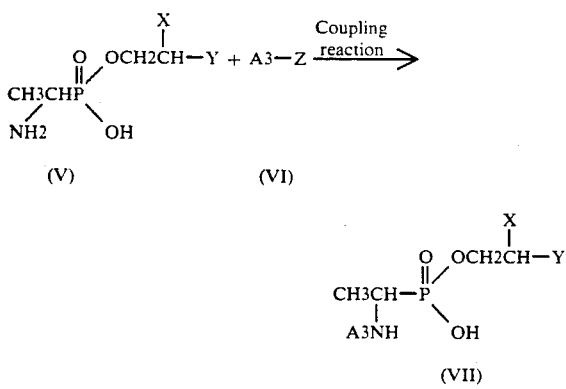

(V)    (VI)

[wherein X has the same definition as the X of the general formula (I) with a proviso that the $A^2$ of the case (c) includes no hydrogen atom and the amino acid or oligopeptide residue has a protecting group; Y has the same definition as the Y of the general formula (I) with a proviso that the B of the case (c) includes no hydroxyl group and the amino acid or oligopeptide residue has a protecting group; $A^3$ is an amino acid or oligopeptide residue obtained by removing, from an amino acid or oliqopeptide having a protecting group, the hydroxyl group of the terminal carboxyl group; and Z is an activated group for the carboxyl group of $A^3$].

In this process, a phosphonic acid represented by the general formula (V) and an active derivative of an amino acid or oligopeptide, represented by the general formula (VI) are reacted to obtain a phosphonic acid derivative represented by the general formula (VII) wherein an amino acid or oligopeptide has been coupled to a phosphonic acid.

The coupling reaction is effected by employing a reaction ordinarily used in peptide chemistry. Explaining a typical case, a phosphonic acid represented by the general formula (V) and a p-nitrophenyl ester of an amino acid or polypeptide, represented by the general formula (VI) are reacted at room temperature in the presence of a base (e.g. triethylamine) using an inert solvent (e.g. dimethyl-formamide) to obtain a desired phosphonic acid derivative represented by the general formula (VII) wherein an amino acid or oligopeptide has been coupled to a phosphonic acid.

Process C

Protecting group-removing reaction

The compound produced according to the process A or B is subjected, if necessary, to a protecting group removing reaction. This reaction is effected by employing a known method. There is employed a method ordinarily used in peptide synthesis chemistry of phosphonic acid synthesis chemistry and suitable for the removal of said protecting group. Examples of the protecting group-removing reagent include catalytic reduction agent, hydrogen bromide-acetic acid, trifluoroacetic acid, conc. hydrochloric acid, dilute hydrochloric acid-acetic acid, formic acid, alkali hydroxide and sodium liquid ammonia. These reagents are selected and used appropriately depending upon the purpose.

When the desired compound obtained is a mineral acid or organic acid salt of an amine, it can be converted to an intramolecular salt.

The separation and purification of the desired product produced according to the process A, B or C requires no special method and can be conducted easily by using well known methods ordinarily used for such purposes, such as solvent extraction, washing. crystallization, ion exchange resin method, normal phase or reversed phase column chromatography.

The pharmaceutical composition of the invention useful in the treatment of antibacterial infections preferably comprises a pharmaceutically acceptable carrier and a pharmaceutically effective amount of an antibacterial compound of formula I.

For administration, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the compounds of the invention.

The present compositions can be administered parenterally and this is preferred when they are used in combination with a carbapenem antibiotic such as imipenem. They may also be administered orally. The compounds of this invention may also be used to treat topical antibacterial infection. Therefore, these compounds may be presented in a number of appropriate dosage forms; e.g., tablets, capsules, suspensions, solutions, and the like, for oral administration; solutions, suspensions, emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be:

(1) suspending agents such as sodium carboxymethylcellulose, methyl cellulose, hydroxypropylmethylcellulose, sodium alginate, polyvinylpyrrolidone, gum tragacanth and gum acacia;

(2) dispersing or wetting agents which may be (a) a naturally-occurring phosphatide such as lecithin, (b) a condensation product of an alkylene oxide with a fatty acid, for example, polyoxyethylene stearate, (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate; or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil in water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3) esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parentally-acceptable diluent or solvent, for example as a solution in 1,3 butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

For topical use, creams, ointments, jellies, solutions or suspensions, etc., containing the compositions of the invention are employed.

Treatment dosage for human beings can be varied as necessary. Generally, oral dosages of the antibacterial compounds of this invention when given orally are in the range 250 mg to 4 g per patient given 3-4 times daily. The intravenous or intramuscular dosages are 100 mg to 1 g given 3-4 times daily. When the compounds of the invention are given intravenously or intramuscularly to potentiate carbapenem antibiotics such as imipenem they are given in combination with the antibiotic in amounts of 0.1-10 mg/kg/day.

The amount of active ingredient that may be combined with the carrier materials to produce a single dosage form will vary depending upon the host treated and the particular mode of administration. For example, a formulation intended for oral administration may contain, for example, from 100 mg to 2000 mg of active agent compounded with an appropriate and convenient amount of carrier material which may vary from about 5 to about 95 percent of the total composition.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The present invention will be explained in more detail below by way of Examples.

EXAMPLE 1

(a) Triazole salt of 2,2-dimethyl-1,3-dioxolane-4-methyl (1RS)-1-carbobenzoxyaminoethylphosphonate To 259 g (10.0 mM) of (1RS)-1-carbobenzoxyaminoethylphosphonic acid were added 100 ml of anhydrous pyridine, 5.03 g (20.0 mM) of mesitylene-sulfonyl triazolide and 1.26 ml (10.0 mM) of 2,2-dimethyl-1,3-dioxolane-4-methanol. They were allowed to stand for 65 hours at room temperature. To the reaction mixture was added 100 ml of ice water, and distillation was conducted to remove the solvent. The residue was purified by means of silica el column chromatography [developing solvent: methylene chloride-methanol (50: 1 by volume)] to obtain 2.52 g (yield: 57%) of the captioned compound as an oily substance.

NMR (CD$_3$OD, $\delta$ ) 1.2-1.8 (9H, m, —CH$_3$×3), 3.6-4.6 (6H, m, CH$_3$C$\underline{H}$—P, O—C$\underline{H}_2$ C$\underline{H}$—C$\underline{H}_2$—), 5.15 (2H, s, —C$\underline{H}_2$Ph), 7.30 (5H, s, —P$\underline{h}$), 8.50 (2H, s, triazole).

(b) 2,3-Dihydroxypropyl (1RS)-1-aminoethylphosphonate hydrochloride 490 mg (1.1 mM) of triazole salt of 2,2-dimethyl-1,3-dioxalane-4-methyl (1RS)-1-carbobenzoxyaminoethylphosphonate was dissolved in a 1:1 (by volume) mixture of methanol and 2 N hydrochloric acid. This solution was stirred for 1 hour at room temperature in the presence of 80 mg of 5% palladium-carbon in a hydrogen current. The catalyst was removed by filtration and the filtrate was subjected to vacuum distillation to dryness. The residue was purified using reversed phase silica gel column chromatography and recrystallized from ethanol to obtain 108 mg (yield: 42%) of the captioned compound as a white crystal. Melting point =215 to 220° C. (decomposed).

NMR (D$_2$O. δ) 1.50 (3H, d.d, J=7Hz, 15Hz, CH$_3$CH—P), 3.4-4.1 (5H, m. 0—C$\underline{H_2}$CHCH$_2$—), 4.3-4.4 (1H, m , —C$\underline{H}$—P).

EXAMPLE 2

(a) Triazole salt of 2,2-dimethyl-1,3-dioxolane-4-methyl (1RS)-1-aminoethylphosphonate 90 ml of methanol was added to 900 mg (2.03 mM) of triazole salt of 2,2-dimethyl-1,3-dioxolane-4 methyl (1RS)-1-carbobenzoxyaminoethylphosphonate. The mixture was stirred for 1 hour at room temperature in the presence of 180 mg of 5% palladium-carbon in a hydrogen current. The catalyst was removed by filtration. The filtrate was subjected to vacuum distillation to dryness to obtain 436 mg (yield: 70%) of the captioned compound.

NMR (CD$_3$OD, δ) 1.3-1.7 (9H, m, —CH$_3 \times 3$) 3.4-4.4 (6H, m, OC$\underline{H_2}$ $\underline{C}$HCH$_2$—, —C$\underline{H}$—P) 8.30 (2H, s, triazole).

(b) 2,2-Dimethyl-1,3-dioxolane- 4-methyl (1RS)-1-[(N-carbobenzox,-1"alan,1)amino]ethylphosphonate In 5 ml of dimethylformamide were dissolved 300 mg (0.97 mM) of triazole salt of 2,2-dimethyl 1,3-dioxolane 4-methyl (1RS)-1-aminoethylphosphonate and 360 mg (1.05 mM) of p-nitrophenyl ester of N-carbobenzoyl-L-alanine. Thereto was added 0.5 ml of triethylamine, and the mixture was stirred for 1 hour at room temperature. The solvent was removed by vacuum distillation. The residue was purified using reversed phase silica gel column chromatography [developing solvent: methanol-water (3:7 by volume)] to obtain 558 mg (yield: 85%) of the captioned compound as an oily substance.

NMR (CD$_3$OD. δ ) 1.1-1.6 (12H, m, —CH$_3 \times 4$), 3.4-4.7 (7H, m, CH$_3$CHCO, —C$\underline{H}$—P, —OC$\underline{H_2}$CHC$\underline{H_2}$—) 5.05 (2H, s, —C$\underline{H_2}$Ph), 7.35 (5H, s, —P$\underline{h}$).

(c) 2,3-Dihydroxypropyl (1RS)-1-(L-alanylamino)ethylphosphonate hydrochloride 558 mg (0.83 mM) of 2.2-dimethyl 1,3 dioxolane 4-methyl (1RS)-1-(N-carbobenzoxyl-L-alanyl)amino]ethylphosphonate was dissolved in a 1:1 (by volume) mixture of methanol and 2 N hydrochloric acid. This solution was stirred for 30 minutes at room temperature in the presence of 50 mg of 5% palladium-carbon in a hydrogen current. The catalyst was removed by filtration. The filtrate was subjected to vacuum distillation to remove the solvent. The residue was purified using reversed phase silica gel column chromatography and recrystallized from ethanol ethyl acetate (1:1 by volume) to obtain 120 mg (yield: 47%) of the captioned compound as a white crystal. Melting point =210° to 215° C. (decomposed)

NMR (D$_2$O. δ ) 1.2-1.6 (6H, m, —CH$_3 \times 2$). 3.5-4.0 (5H, m, 0—C$\underline{H_2}$CHCH$_2$), 4.0-4.2 (2H, m, CH$_3$CHCO.—C$\underline{H}$—P).

EXAMPLE 3

2,3-Dipalmitoyloxypropyl (1RS)-1-carbobenzoxyamino ethylphosphonate

To 18 ml of a solution of 1.00 g (1.76 mM) of DL-1,2-dipalmitin and 456 mg (1.76 mM) of (1RS)-1-carbobenzoxyaminoethylphosphonic acid in anhydrous pyridine was added 885 mg (3.52 mM) of mesitylenesulfonyl triazolide. The mixture was allowed to stand for 28 hours at room temperature. 18 Ml of ice water was added to the reaction mixture. The solvent was removed by vacuum distillation. The residue was dissolved in methylene chloride. The solution was washed with 5% hydrochloric acid, dried with Na$_2$SO$_4$ and subjected to vacuum distillation to remove the solvent. The residue was purified by means of silica gel column chromatography [developing solvent: methylene chloride-methanol (20:1 by volume)]to obtain 840 mg (yield: 59%) of the captioned compound as a white powder.

NMR (CDCl$_3$, 6) 0.7-2.5 (65H, m, —(CH$_2$)14CH$_3 \times 2$, CH$_3$CH—P) 3.6-4.4 (6H, m, 0—C$\underline{H_2}$CHC$\underline{H_2}$, CH$_3$CH—P), 5.05 (2H, s, —C$\underline{H}$Ph), 7.20 (5$\underline{H}$, s, —P$\underline{h}$).

EXAMPLE 4

2,3-Dipalmitoyloxypropyl (1RS)-1-aminoethylphosphonate 840 mg (1.04 mM) of 2,3-dipalmitoyloxypropyl (1RS)-1-carbobenzoxyaminoethyl phosphonate was dissolved in 150 ml of a 2:1 (by volume) mixture of tetrahydrofuran and ethyl acetate. The solution was stirred for 4 hours at room temperature in the presence of 1 g of 5% palladium carbon in a hydrogen current. The catalyst was removed by filtration. The filtrate was evaporated to dryness. The residue was recrystallized from methanol to obtain 260 mg (yield: 37%) of the captioned compound as a white crystal. Melting point =153° to 155° C. IR (KBr, cm$^{-1}$) 1740, NMR (CDCl$_3$, δ ) 0.7-2.4 (65H, m, —(CH$_2$)14CH$_3 \times 2$, CH$_3$C$\underline{H}$—P). 3.6-4.4 (6H, m, O—C$\underline{H_2}$C$\underline{H}$C$\underline{H_2}$, $\overline{C}$H$_3$C$\underline{H}$—P).

EXAMPLE 5

(2R)-2-Carbobenzoxyamino-2-(p-nitrobenzyloxycarbonyl)ethyl (1RS)-1-carbobenzoxyaminoethylphosphonate To 20 ml of a solution of 2.10 g (8.10 mM) of (1RS) 1-carbobenzoxyaminoethylphosphonic acid and 3.00 g (8.01 mM) of p-nitrobenzyl ester of N-carbobenzoxy-D-serine in pyridine was added 4.10 g (16.3 mM) of mesitylenesulfonyl triazolide. The mixture was stirred for 26 hours at room temperature. 10 Ml of water was added to the reaction mixture with ice-cooling. The mixture was concentrated under vacuum. The residue was purified using silica gel column chromatography [developing solvent: chloroformmethanol (50:1 5:1 by volume)]. The resulting oily substance was dissolved in chloroform. The solution was washed with 5% hydrochloric acid and water in this order, dried with MgSO$_4$ and then subjected to vacuum distillation to remove the solvent. The residue was recrystallized from ethyl acetate and n-hexane to obtain 2.63 g (yield: 53%) of the captioned compound as a gel-like substance. Melting point=153° to 158° C. NMR (CDCl₃+CD₃OD, δ) 1.35 (3H,d.d, J=16Hz, 8Hz, CH₃CH—P), 3,80-4.80 (4H,m, —CH—P, O—CH₂CH—CO), 4.95-5.30 (6H, m, —CH₂Ph×3), 7.30 (1OH, s×2, —Ph×2), 7.50 (2H, d, J=8Hz,

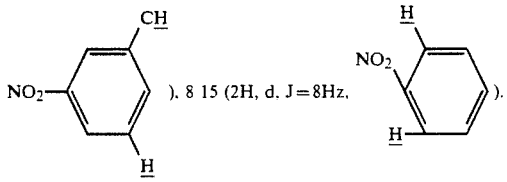). 8 15 (2H, d. J=8Hz,).

EXAMPLE 6

(2R)-2-Amino-2-carboxyethyl (1RS)-1-aminoethylphosphonate hydrochloride

To 100 ml of a suspension of 1.00 g (1.62 mM) of (2R)-2-carbobenzoxyamino-2-(p-nitrobenzyloxycarbonyl) ethyl-(1RS)-1-carbobenzoxyaminoethylphosphonate in methanol were added 5.0 ml (5.0 mM) of 1 N hydrochloric acid and 700 mg of palladium black. The mixture was stirred for 6 hours at room temperature in a hydrogen current. The catalyst was removed by filtration. The filtrate was subjected to vacuum distillation to dryness. The residue was purified using reversed phase silica gel column chromatography (developing solvent: water) and recrystallized from ethanol to obtain 352 mg (yield: 87%) of the captioned compound as a gel-like (decomposed)

IR (KBr, cm⁻¹) 1720.

NMR (CD₃OD, δ ) 1.50 (3H, d.d, J=16Hz, 8Hz, CH₃CH—P) 0.20-3.60 (1H, m, —CH—P), 4.20-4.50 (3H, m, OCH₂CHCO).

EXAMPLE 7

(2S)-2-(tert-butoxycarbonylamino)-2-(1S)-1-tertbutoxycarbonylethylaminocarbonyl)ethyl(1RS)-1-carbobenzoxyaminoethylphosphonate To 25 ml of a solution of 1.30 g (5.02 mM) of (1RS)-1-carbobenzoxyaminoethylphosphonic acid and 1.70 g (5.11 mM) of tert butyl ester of N-(N-tert-butoxycarbonyl-1-seryl)-L-alanine in pyridine was added 2.60 g (10.3 mM) of mesitylenesulfonyl triazolide. The mixture was stirred for 25 hours at room temperature. 10 Ml of water was added to the reaction mixture under ice-cooling and the whole mixture was concentrated under vacuum. The residue was purified by means of silica gel column chromatography [developing solvent: chloroformmethanol-triethylamine (50:1:0.01-10:1:0.01)]. The resulting oily substance was dissolved in chloroform. The solution was washed with 5% hydrochloric acid and water in this order, dried with MgSO₄ and subjected to vacuum distillation to remove the solvent, whereby 1.92 g (yield: 67%) of the captioned compound was obtained as an oily substance.

NMR (CDCl₃+CD₃OD, δ) 1.20-1.60 (24H, m, C(CH₃)₃×2, —CH₃×2), 3.80-4.50 (5H, m, O—CH₂CHCON,CHCO, CH₃CH—P). 5.10 (2H, s, —CH₂Ph), 7.25 (5H, s, —Ph).

EXAMPLE 8

(2S)-2-amino-2-((1S)-1-carboxyethylaminocarbonyl)ethyl (1RS)-1-aminoethylphosphonate monohydrobromide 12 Ml of acetic acid solution saturated with hydrogen bromide was added, with ice-cooling, to 628 mg of (2S)-2 (tert-butoxycarbonylamino)-2-((1S)-1-tert-butoxycarbonylethylaminocarbonyl)-ethyl (1RS)-1-carbobenzoxyaminoethylphosphonate. The mixture was stirred for 2 hours. 70 Ml of ether was added to the reaction mixture. The resulting gel-like substance was collected by filtration, purified using reversed phase silica gel column chromatography (developing solvent: water) and then recrystallized from acetone to obtain 303 mg (yield: 76%) of the captioned compound as a gel-like substance. Melting point =155° to 173° C. (decomposed)

IR (KBr, cm⁻¹) 1720, 1680.

NMR (D₂O+NaOD, δ ) 1.20 (3H, d.d, J=14Hz, 7Hz, CH₃CH—P), 1.30 (3H, d, J=7Hz, CH₃CHCO) 2.70-3.10 (1H, m, CH₃CH—P), 3.65 (1H, t, J=5Hz,

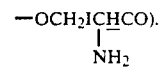

4.05 (2H, d, J=5Hz,

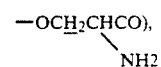

4.20 (1H, q, J=7Hz,

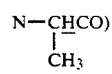

EXAMPLE 9

(2S)-2-(tert-butoxycarbonyl-L-alanylamino)-2-(tert-butoxycarbonyl)ethyl-(1RS)-1-carbobenzoxyaminoethylphosphonate To 20 ml of a solution of 780 mg (3.01 mM) of (1RS)-1-carbobenzoxyaminoethylphosphonic acid and 1.00 g (3.01 mM) of tert-butyl ester of N-(N-tert butoxycarbonyl-1-alanyl)-L-serine was added 1.51 g (6.01 mM) of mesitylenesulfonyl triazolide. The mixture was stirred for 21 hours at room temperature. 10 Ml of water was added to the reaction mixture with ice-cooling. The whole mixture was concentrated under vacuum. The residue was purified using silica el column chromatography [developing solvent: chloroform-methanol-triethylamine (50:1:0.01 0:1:0.01)]. The resulting oily substance was dissolved in chloroform. The solution was washed with 5% hydrochloric acid and water in this order, dried with MgSO₄ and then subjected to vacuum distillation to remove the solvent, whereby 1.54 g (yield: 89%) of the captioned compound was obtained as an oily substance.

NMR (CDCl₃ δ ) 1.00-1.60 (24H, m, C(CH₃)₃ ×2, —CH₃×2), 3.80-4.70 (5H, m,

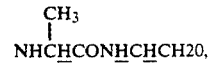

$CH_3$—CH—P), 5.10 (2H, s, —CH$_2$Ph), 7.30 (5H, s, —Ph).

EXAMPLE 10

(2S)-2-(L-alanylamino)-2-carboxyethyl-(1RS)-1-aminoethylphosphonate monohydrobromide 81 Ml of an acetic acid solution saturated with hydrogen bromide was added, with ice-cooling, to 600 mg (1.05 mM) of (2S) 2 (tert butoxycarbonyl-L-alanylamino)-2-(tert-butoxycarbonyl)-ethyl-(1RS)-1-carbobenzoxyamino-ethylphosphonate. The mixture was stirred for 1 hour. 70 Ml of ether was added to the reaction mixture. The resulting gel-like substance was collected by filtration, purified by means of reversed phase silic gel column chromatography (developing solvent: water) and then recrystallized from acetone to obtain 239 mg (yield: 63%) of the captioned compound as a gel-like substance. Melting point =152° to 165° C. (decomposed).

IR (KBr, cm$^{-1}$) 1720, 1680.

NMR (D$_{20}$+NaOD, δ) 1.25 (3H, d.d, J=14Hz, 7Hz, CH$_3$CH—P), 1.30 (3H, d, J=7Hz, CH$_3$CHCO), 2.80–3.10 (1H, m, CH$_3$CH—P), 3.60 (1H, q, J=7Hz, CH$_3$CHCO), 4.10-4.35 (2H, m, OCH$_2$CH—N), 4.40-4.55 (1H, m, OCH$_2$CHCO).

What is claimed is:

1. A compound represented by the Formula (I):

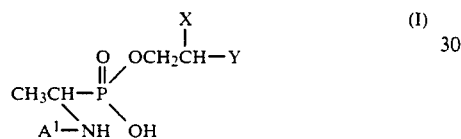

wherein A$^1$ is a hydrogen atom, or, a residue consisting of one or two amino acids optionally having a protecting group which is obtained by removing, from an oligopeptide optionally having a protecting group, the hydroxy group of the terminal carboxyl group; X is (a) a hydroxyl group,

wherein R$^1$ is an alkyl group, or (c) —NHA$^2$ wherein A$^2$ is a hydrogen atom, or a residue consisting of one or two amino acids optionally having a protecting group which is obtained by removing, from the amino acid or dipeptide optionally having a protecting group, the hydroxyl group of the terminal carboxyl group, or a protecting group for the amino group; and Y is (a) —CH$_2$OH,

wherein R$^2$ is an alkyl group, or

wherein B is a hydroxyl group, or a residue consisting of one or two amino acids optionally having a protecting group obtained by removing, from the amino acid or dipeptide optionally having a protecting group, the hydrogen atom of the terminal group, or a protecting group for the carboxyl group provided that at least one of A$^1$, A$^2$, or B is a dipeptide residue.

2. The compound according to claim 1, wherein A$^1$ is a hydrogen atom, or a residue consisting of one or two amino acids selected from glycine, alanine, valine, norvaline, leucine, isoleucine, serine, threonine, phenylalanine, tyrosine, tryptophan, histidine, aspartic acid, asparagine, glutamic acid, glutamine, lysine, arginine, cysteine, methionine and proline, optionally having a protecting group for carboxyl group selected from C$_1$-C$_5$ lower alkoxy and aryloxy; X is (a) —OH

wherein R$^1$ is C$_1$-C$_{30}$ alkyl group, or (c) —NHA$^2$, A$^2$ is the same as the definition of A$^1$ mentioned above, but, A$^1$ and A$^2$ are independent of each other; and Y is (a) —CH$_2$OH,

R$^2$ is C$_1$-C$_{30}$ alkyl group, or

B is —OH, or a residue consisting of one or two amino acids selected from glycine, alanine, valine, norvaline, leucine, isoleucine, serine, threonine, phenylalanine, tyrosine, tryptophan, histidine, aspartic acid, asparagine, glutamic acid, glutamine, lysine, arginine, cysteine methionine, optionally having a protecting group for carboxy group selected from C$_1$-C$_5$ lower alkoxy group, and aryloxy group.

3. The compound according to claim 1, wherein A$^1$ is a hydrogen atom, or a residue consisting of one or two amino acids selected from glycine, alanine, valine, norvaline, leucine, isoleucine, serine, cysteine and methionine, optionally having a protecting group for carboxyl group selected from C$_1$-C$_5$ lower alkoxy, methoxymethyloxy, acetoxymethyloxy, pivaloyloxymethyloxy, benzyloxy, p-nitrobenzyloxy, p-methoxybenzyloxy, phthlidyloxy and aryloxy; X is (a) —OH,

R$^1$ is C$_1$-C$_{30}$ alkyl group, or (c) —NHA$^2$, A$^2$ is the same as the definition of A$^1$ mentioned above, but A$^1$ and A$^2$ are independent of each other; and Y is (a) —CH$_2$OH, (b) —CH$_2$OC(O)R$^2$, R$^2$ is C$_1$-C$_{30}$ alkyl group, or

(c)

B is —OH, or a residue consisting of one or two amino acids selected from glycine, alanine, valine, norvaline, leucine, isoleucine, serine, cysteine, methionine optionally having a protecting group for carboxyl group selected from $C_1$–$C_5$ lower alkoxy, methoxymethyloxy, acetoxymethyloxy, pivaloyloxymethyloxy, benzyloxy, p-nitrobenzyloxy, p-methoxybenzyloxy, phthlidyloxy and aryloxy.

4. The compound according to claim 1, wherein $A^1$ is a hydrogen atom, or a residue consisting of one or two amino acids selected from glycine, alanine, valine, norvaline, leucine, isoleucine, serine, cysteine methionine, optionally having a protecting group for carboxyl group selected from methoxy, ethoxy, propoxy, tert-butoxy, methoxymethyloxy, acetoxymethyloxy, pivaloyloxymethyloxy, benzyloxy, p-nitrobenzyloxy, p-methoxybenzyloxy, phthlidyloxy, phenyloxy and indanyloxy; S is (a) —OH

(b)

$R^1$ is $C_1$–$C_{30}$ alkyl group, or (c) —$NHA^2$, $A^2$ is the same as the definition of $A^1$ mentioned above, but $A^1$ and $A^2$ are independent of each other; and Y is (a) —$CH_2OH$,

(b)

$R^2$ is $C_1$–$C_{30}$ alkyl group, or

(c)

B is —OH, or a residue consisting of one or two amino acids selected from glycine, alanine, valine, norvaline, leucine, isoleucine, serine, cysteine, and methionine, optionally having a protecting group for the carboxyl group selected from methoxy, ethoxy, propoxy, tert-butoxy, methoxymethyloxy, acetoxymethyloxy, pivaloyloxymethyloxy, benzyloxy, p-nitrobenzyloxy, p-methoxybenzyloxy, phthalidyloxy, phenyloxy and indanyloxy.

* * * * *

UNITED STATES PATENT AND TRADEMARK OFFICE
CERTIFICATE OF CORRECTION

PATENT NO.  : 5,151,521

DATED       : September 29, 1992

INVENTOR(S) : Y. Morita, et al.

It is certified that error appears in the above-identified patent and that said Letters Patent is hereby corrected as shown below:

At claim 4, column 15, line 21, between the words "cysteine methionine", please add the word -- and --.

At claim 4, line 29, please delete the letter "S" and replace it with the letter -- X --.

Signed and Sealed this

Twenty-eighth Day of September, 1993

Attest:

BRUCE LEHMAN

Attesting Officer

Commissioner of Patents and Trademarks